United States Patent
Mountz et al.

(10) Patent No.: US 6,419,919 B2
(45) Date of Patent: *Jul. 16, 2002

(54) METHOD FOR THE AUGMENTATION OF GENE EXPRESSION

(76) Inventors: John D. Mountz, 2806 Vestavia Forest Pl., Birmingham, AL (US) 35299; Huang-Ge Zhang, 3240 Tyrol Rd., Birmingham, AL (US) 35216; Tong Zhou, 332 W. Stonebrook Pl., Birmingham, AL (US) 35226; Carl K. Edwards, III, 1620 Pitkin Ave., Superior, CO (US) 80027

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,952

(22) Filed: Nov. 6, 1998

Related U.S. Application Data (60) Provisional application No. 60/064,694, filed on Nov. 7, 1997, now abandoned.

(51) Int. Cl.[7] .................. A01N 43/04; A01N 37/18; C12N 15/63; A61K 39/00; C07K 1/00

(52) U.S. Cl. ................... 424/93.2; 514/2; 514/44; 435/320.1; 435/325; 435/455; 424/185.1; 530/351

(58) Field of Search .................... 514/44, 2; 435/320.1, 435/325, 455; 424/93.2, 185.1; 530/351

(56) References Cited

PUBLICATIONS

Verma et al Nature 389:239–242, 1997.*
Worgall et al, Hu. Gene Ther. 8:37–44, 1997.*
Zhang et al, Hu Gene Ther. 9:1875–184, 1998, 1997.*

* cited by examiner

*Primary Examiner*—Scott D. Priebe
*Assistant Examiner*—Sumesh Kaushal
(74) *Attorney, Agent, or Firm*—Benjamin Aaron Adler (57) ABSTRACT

The present invention provides a method of increasing adenoviral gene expression in a tissue of an animal, comprising the step of administering to said animal a pharmacologically effective dose of tumor necrosis factor binding protein. Also provided is a various method of method of reducing an inflammatory response associated with adenoviral administration in a tissue of an animal, comprising the step of administering to said animal a pharmacologically effective dose of tumor necrosis factor binding protein.

12 Claims, 9 Drawing Sheets

(4 of 9 Drawing Sheet(s) Filed in Color)

METHOD FOR THE AUGMENTATION OF GENE EXPRESSION

CROSS-REFERENCE TO RELATED APPLICATION

This application claims the benefit of U.S. provisional application Serial No. 60/064,694, filed Nov. 7, 1997, now abandoned.

FEDERAL FUNDING LEGEND

This invention was created in part using funds from the National Institutes of Health under grants N01-AR-62224, P50 AI23649, R01-AR42547. The federal government, therefore, has certain rights in this invention.

BACKGROUND OF THE INVENTION

1. Field of the Invention

The present invention relates generally to the fields of immunology and protein chemistry. More specifically, the present invention relates to the prolongation of gene therapy and the inhibition of inflammation decreasing the activity of TNF.

2. Description of the Related Art

The immune response to adenovirus vectors has been recognized as a limiting factor in the successful application of gene therapies. Cellular and humoral immune responses have been implicated in the shortened time-span of transgene expression, the eradication of transfected cells, and the preclusion of the opportunity to re-administer the adenovirus (Yang et al.,1996b; Kass-Eisler et al.,1996; Yang et al., 1996c; Yang and Wilson, 1995c). Immunosuppressive drugs, including cyclophosphamide, FK506, and cyclosporine reduce this immune response (Jooss et al.,1996; Vilquin et al., 1995). Other strategies reported to control the immune response include reduction of the T-cell response by anti-T cell therapy (Sawchuk et al.,1996) and anti-CD4 monoclonal antibodies (Dematteo et al.,1996), reduction of co-stimulatory activity using CTLA4-Ig (Guerette et al., 1996; He et al., 1996; Kay et al., 1997), and induction of intrathymic tolerance (Ilan et al., 1996). B-cell activation production of neutralizing antibody production is decreased after treatment with anti-CD40 (Yang et al., 1996a) and deoxyyspergualin (Smith et al., 1996). In addition, modification of adenovirus vectors may be effective in reducing the immune response (Gao et al., 1996; Fisher et al., 1997).

Antigen presenting cells (APCs) play an important role in both specific and non-specific immune responses to adenovirus. Processing of the antigen, presentation of the antigen in the context of major histocompatibility complex (MHC) class I molecules, and cytokine production by the antigen presenting cells contribute to the immune response to adenovirus (Yang et al., 1995a; Schowalter et al., 1997). The E19 adenovirus gene product leads to decreased MHC class I antigen expression and an immune response to this gene product occurs in class I mutant mice indicating that MHC class I antigen expression is not required.

Interleukin-12 (IL-12) and other cytokines, such as interferon-γ (IFN-γ), are expressed at high levels early after adenovirus infection and it has been proposed that these evoke a TH1-type response to adenovirus (Yang et al., 1995b; Coutelier et al., 1995; Day et al., 1994). The role of TNF-α production by antigen presenting cells in the early inflammatory immune response to adenovirus is less well understood (Smith et al., 1994). TNF-α increases expression of the adenovirus E3 proteins, which, in turn, protects the cells from the lytic activity of TNF-α. These finding demonstrate the central role for neutralization of TNF-α for the virus to survive (Deryckere et al., 1995; Tufariello et al., 1994; Ranheim et al., 1993; Korner et al., 1992; Wold, 1993).

TNF-α acts by crosslinking either the high affinity receptor p55 TNF-RI or the low affinity p75 TNF-RII, the TNF-RI being most closely associated with inflammatory responses (Smith et al., 1994). The effectiveness of TNF-α antagonists, such as sTNF receptor (sTNFR) inhibitors, in ameliorating inflammation of the lung has been demonstrated in acute lung injury, which frequently develops following hemorrhage and is characterized by increased proinflammatory cytokine levels and massive neutrophil accumulation in the lung (Abraham et al., 1994; Su et al., 1998; Rabinovici et al., 1996). A rapid increase in the level of TNF-α mRNA expression among pulmonary cell populations precedes the development of acute lung injury. In mice, therapy with sTNFR:Fc, composed of soluble dimeric human p80 TNF-R linked to the Fc region of human IgG1, prevents the post-hemorrhage increases in circulating and pulmonary TNF-α levels and diminishes the increase in IL1β, IL6, TNF-α and IFN-γ mRNA (Haak-Frendscho et al., 1994; Fisher et al., 1996; Wooley et al.,1993; Kolls et al.,1994).

A novel TNF-binding protein (TNF-bp) has been developed which is composed of a polyethylene glycol (PEG)-linked dimer of the recombinant human TNF-RI soluble receptor, and is capable of binding to TNF-α with high affinity (Evans et al.,1996). The use of the TNF-bp PEG-linked dimer has potential therapeutic advantages over the use of monomeric TNF-bp. First, dimerization of TNF-bp enhances the avidity for TNF-α, and the resultant mobilization of two sites within the TNF-α trimer may prevent TNF-α-mediated signal transduction since cross-linking of two TNF-Rs by TNF is required to trigger cellular responses (Evans et al., 1996). Second, the PEG-linked dimer has a large molecular mass with a predictably slow clearance, which allows relatively infrequent dosing. Third, the PEG-linked dimer may exhibit lower immunogenicity than the pure protein since it has been reported that PEG conjugation to proteins leads to lowered antibody response (Delgado et al., 1992; Katre 1990).

The prior art is deficient in the lack of effective means for the prolongation of gene therapy expression. The present invention fulfills this longstanding need and desire in the art.

SUMMARY OF THE INVENTION

The present studies indicate that there is greatly decreased inflammatory disease and prolonged gene therapy expression in AdCMVlacZ virus-infected mice treated with TNF-bp compared with vehicle-treated mice. These results indicate that TNF-α is a key factor in the pathogenesis of inflammation in AdCMVlacZ-virus infected mice. Thus, TNF-bp PEG-linked dimer may be therapeutically useful in reducing the inflammatory response to adenovirus gene therapy.

The clinical application of adenoviral gene therapy is impeded currently by the potent host immune response to the virus that limits the duration of its effects. These studies showed the role of TNF-α on the inflammatory response and expression of a lacZ expressing adenovirus in the lung and liver of mice after administration of recombinant adenovirus using soluble TNF receptor (TNF-bp). The mononuclear cell inflammatory response was determined histologically at different times after intranasal or intravenous administration of a recombinant adenovirus expressing the lacZmarker gene. The expression of the activity of the lacZ gene product of the adenovirus. Treatment with TNF-bp reduced circulating levels of TNF-α, greatly reduced the inflammatory response, and resulted in prolonged expression of lacZ for up to 30 days in the lung and liver after either intranasal or intravenous administration of adenovirus. Both intranasal and intravenous administration of adenovirus to vehicle-treated C57BL/6-+/+ mice resulted in a persistent inflammatory response and clearance of the adenovirus in the lung. However, clearance of the virus also was observed in the liver, despite a minimal inflammatory response. These results indicate that TNF-α is the primary factor driving the inflammatory response and leading to elimination of adenovirus-infected cells in the lung and liver as TNF-bp was capable of inhibiting these effects.

In one embodiment of the present invention, there is provided a method of increasing adenoviral gene expression in a tissue of an animal, comprising the step of administering to said animal a pharmacologically effective dose of tumor necrosis factor binding protein.

In another embodiment of the present invention, there is provided a method of reducing an inflammatory response associated with adenoviral administration in a tissue of an animal, comprising the step of administering to said animal a pharmacologically effective dose of tumor necrosis factor binding protein.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains at least one drawing executed in color. Copies of this patent with color drawings are provided to the Patent and Trademark Office with payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the effect of TNF-bp treatment on serum levels of TNF. ELISA assays were carried out for determination of TNF-α level in normal C57BL/6-+/+ mice. AdCMVlacZ virus-infected vehicle-treated mice and AdCMVlacZ virus-infected mice treated with TNF-bp. Serum TNF level was determined using a standard curve. A total of 10 vehicle-control, and 18 TNF-bp treated AdCMVlacZ ($1\times10^{10}$ p.f.u.) virus-infected mice were analyzed at 24 and 48 hours after I.V. infection.

FIG. 2A shows that the lungs of vehicle-treated AdCMVlacZ virus-infected mice had typical inflammation characterized by mononuclear cell infiltration in the interstitium and dilation of bronchioles, whereas the lungs from TNF-bp treated AdCMVlacZ virus infected mice were relatively normal with normal thickness of alveolar walls, normal space of alveoli, and normal diameter of bronchioles. FIG. 2B shows the frozen sections prepared for analysis of β-Gal staining. (Magnification×320).

FIG. 3A: The livers of vehicle-treated AdCMVlacZ virus-infected mice had inflammation characterized by mononuclear cell infiltration around the portal vein, whereas the livers from AdCMVlacZ virus infected mice treated with TNF-bp were relatively normal. FIG. 3B Frozen sections were prepared for analysis of β-Gal staining. (Magnification×320).

FIG. 7 shows the cytotoxic T cell and anti-adenovirus antibody response after intravenous administration of AdCMVlacZ. The cytotoxic and antibody responses were determined in control mice, in mice treated with AdCMVlacZ and in mice treated with AdCMVlacZ plus TNF-bp. For the anti-adenovirus antibody response, the results represent the mean±SEM of five mice analyzed separately.

DETAILED DESCRIPTION OF THE INVENTION

The following abbreviations may be used herein: AdCMVlacZ: adenovirus with recombinant LacZ driven by cytomegalovirus promoter; TNF-R: TNF receptor; PEG: polyethylene glycol; TNF-bp: TNF binding protein The present invention is directed to a method of increasing adenoviral gene expression in a tissue of an animal, comprising the step of administering to said animal a pharmacologically effective dose of tumor necrosis factor binding protein. In one embodiment, the tumor necrosis factor binding protein is a polyethylene glycol-linked dimer of tumor necrosis factor binding protein. Preferably, the tumor necrosis factor binding protein is administered in a dose of from about 0.3 mg/kg to about 5.0 mg/kg. Although the tumor necrosis factor binding protein can be administered in any acceptable fashion, it is preferably is administered intranasally or intravenously. The tumor necrosis factor binding protein results in a decrease in serum tumor necrosis factor-α.

The present invention is directed to a method of reducing an inflammatory response associated with adenoviral administration in a tissue of an animal, comprising the step of administering to said animal a pharmacologically effective dose of tumor necrosis factor binding protein such that said tumor necrosis factor binding protein inhibits an inflammatory response in said animal. In one embodiment, the tumor necrosis factor binding protein is a polyethylene glycol-linked dimer of tumor necrosis factor binding protein. Preferably, the tumor necrosis factor binding protein is administered in a dose of from about 0.3 mg/kg to about 5.0 mg/kg. Although the tumor necrosis factor binding protein can be administered in any acceptable fashion, it is preferably is administered intranasally or intravenously. The tumor necrosis factor binding protein results in a decrease in serum tumor necrosis factor-α.

It is specifically contemplated that pharmaceutical compositions may be prepared using the tumor necrosis factor binding protein. In such a case, the pharmaceutical composition comprises the tumor necrosis factor binding protein and a pharmaceutically acceptable carrier. A person having ordinary skill in this art would readily be able to determine, without undue experimentation, the appropriate dosages and routes of administration of the tumor necrosis factor binding protein.

As is well known by those having ordinary skill in this art, modified versions of tumor necrosis factor binding protein would likely be very useful. Representative examples of useful versions of tumor necrosis factor binding protein include soluble TNFRI or TNFbp or modified TNFR such as the 2.6 domain TNFRI.

As is well known by those having ordinary skill in this art, one could exploit the present invention using well known gene therapy techniques. For example, the tumor necrosis factor binding protein, or a modification thereof, could be ligated into an adenovirus in combination with a therapeutic gene. The inclusion of the tumor necrosis factor binding protein would neutralize TNFα resulting in enhanced expression of the therapeutic gene.

The effectiveness of neutralization of TNF-α with a sTNFRI in the inhibition of inflammation and prolongation of LacZ expression after adenovirus-LacZ gene therapy was examined. sTNFRI reduced serum TNF-α to undetectable levels after adenovirus administration, decreased pulmonary and liver inflammatory response, and enhanced expression of the lacZ gene. There results indicate that treatment with a sTNFRI during gene therapy administration may be efficacious in minimizing the inflammatory response and increasing gene therapy efficacy.

The following examples are given for the purpose of illustrating various embodiments of the invention and are not meant to limit the present invention in any fashion.

EXAMPLE 1
Mice

C57BL/6-+/+ mice were purchased from Jackson Laboratory (Bar Harbor, Me.). The cages, bedding, water, and food were sterilized, and the mice were handled with aseptic gloves. Mice were housed in groups of 3–4 mice per cage for the duration of the experiment. Female mice were used at 8 weeks of age.

EXAMPLE 2
Preparation and Administration of the Replicative-defective AdCMVlacZ Recombinant Virus The recombinant adenovirus-LacZ driven by the CMV promoter (AdCMVlacZ) was generated employing the recombination of the two plasmids as described (Graham and Prevec, 1995). Briefly, the PCR-amplified *Escherichia coli* LacZ gene from pcDNA$_3$ His (Invitrogen) was inserted directionally into the adenoviral shuttle vector pCA13 (Microbix, Inc., Canada) resulting in pCA13 LacZ. The pCA13 lacZ gene was then co-transfected with pJM17 (Microbix, Inc., Canada) into 293 cells using the lipofectin method as described in the manufacturer's manual (Gibco, BRL). The recombinant virus was picked after staining with x-gal followed by three rounds of plaque purification. AdCMV/lacZ recombinant virus ($1 \times 10^{10}$ p.f.u.) was administered either intranasally or intravenously as described previously. Intravenous administration of adenovirus has been shown to result in wide dissemination with high tropism for liver and lung. Intranasal (I.N.) administration was carried out by placing $0.5 \times 10^{10}$ p.f.u. of adenovirus in 15 (1 PSB into each nostril of mice. Mice were examined on days 0, 3, 7, 21, and 30 after administration of AdCMVlacZ recombinant virus.

EXAMPLE 3
Administration of TNF-binding Protein

Mice were treated with three doses of TNF-binding protein (5 mg/kg body weight, intraperitoneally, every other day) on days −1, +1, and +3 relative to gene therapy administration. TNF-bp is a pegylated dimer that tightly binds trimeric TNF-α with a dissociation constant $K_d$ of $10^{-9}$ compared with its dissociation constant for sTNF-RII:Fc ($K_d$ fo $10^{-7}$). TNF is sequestered both functionally and immunigenically by the TNF-bp. Therefore, the dissociation half-life for TNF-α with TNF-bp is 2.5 days whereas the on-off rate for TNF association with sTNF-RII is approximately 18 minutes. TNF-α is no longer detectable by enzyme linked immunosorbent assay (ELISA) after binding of TNF-bp, as described in the present experiment. Therefore, in the serum, any free TNF would be expected to be bound to TNF-bp and therefore not detectable by ELISA and also would not be available as a physiologic cytokine.

EXAMPLE 4
Histologic Analysis

Lung and liver were dissected from mice sacrificed by cervical dislocation. Tissues were fixed in 10% formalin and embedded in paraffin. Sections (4.0 μm) were obtained from the paraffin-embedded tissue samples and stained with hematoxylin and eosin. Ten sections of lung and liver tissue per mouse were examined and graded for mononuclear cell infiltration on a scale from 0 (not present) to 4+ (maximum severity). The cellularity infiltration scale included both mononuclear cells (PMNs), which represented less that 10% of the infiltrated cells on day 3, and no PMNs were visible on day 30 either after intranasal or intravenous administration of adenovirus.

EXAMPLE 5
Measurement of β-Gal Expression

The in vivo duration of lacZ gene expression was determined by histologic evaluation of fixed tissue sections as described (Wright et al., 1997). The lung and liver were snap-frozen in liquid nitrogen followed by serial transverse sectioning (10.0 μm). The sections were then fixed in 0.5% glutaraldehyde in PBS, pH 7.4, followed by staining in x-gal solution for 2 hours at 37° C. The sections were examined microscopically and scored for percentage of cells expressing β-Gal using the following scale: 0=<1%, 1⁺=<5%, 2⁺=<10%, 3⁺=<25% and 4⁺=>50%.

EXAMPLE 6

Quantitation of β-galactosidase Expression in Liver

β-galactosidase activity was determined as described (Young et al., 1993). Freshly isolated liver and lung tissue was homogenization for 20 seconds in a tissumizer in 1 ml of β-gal buffer (Tropix, Inc., Bedford Mass.). The homogenate was centrifuged at 12,500×g for 10 minutes at 4° C., and the supernatant was heated for 60 minutes at 48° C. to inactivate the endogenous eukaryotic β-galactosidase activity. The sample was then centrifuged at 12,500×g for 5 min, and 10 μl of the supernatant was assayed for β-galactosidase activity using the Galacto-light™ (Tropix, Inc., Bedford Mass.) chemi-luminescent reporter assay. The reaction was carried out for 10 minutes at room temperature (RT) and β-galactosidase activity was assayed using a luminomiter (Monolight 500). The protein concentration was determined by the Bradford assay. The activity is expressed as the relative light units/min/mg of total protein in the liver or lung.

EXAMPLE 7

Measurement of Serum TNF-α and Statistical Analysis

The concentration of TNFα in serum samples obtained from mice by retroorbital sinus puncture was measured using an ELISA assay kit according to the procedure recommended by the supplier (Endogen, Cambridge, Mass.).

The Student's t-test was used for statistical analysis when two different groups of samples were compared. A p value of less than 0.05 was considered statistically significant.

EXAMPLE 8

ELISA for Anti-adenovirus Antibody Production

ELISA plates were coated with a guinea pig polyclonal anti-adenovirus (Ad) antibody. Viable AdCMVlacZ (10⁹ PFU) was added for 30 minutes at 4 C. and the plates were washed three times. Serum samples were diluted 1:1000, and incubated for 30 minutes at 4 C. After washing, a peroxidase-conjugated anti-mouse IgG (Southern Biotechnology Associates, Birmingham Ala.) was added followed by washing and development with the tetramethylbenzidine (TMB) (Sigma, St. Louis, Mo.) substrate. The optical density (OD) was determined at 405 nm on a microplate reader (Emas; Molecular Devices, Menlo Park Calif.). Each sample was assayed in duplicate and the average optical density reading from the duplicates of each sample was then obtained. At least three mice were tested in each group.

EXAMPLE 9

Analysis of Anti-adenovirus Cytotoxic T Cells

Cytotoxic T cell activity was estimated by measuring the ability of the test cells to induce cytotoxicity of AdCMVlacZ-infected C57BL/6 antigen presenting target cells. The AdCMVlacZ-infected C57BL/6-lpr/lpr macrophage cell line was labeled with 700 uCi of Na$^{51}$CrO$_2$ (Amersham, Arlington Heights, Ill.) for 1 hour at 37 C. The cells were then washed three times in RPMI 1640 medium supplemented with dialyzed 10% fetal calf serum (FCS). The target cells were added to purified splenic T cells from day-16 AdCMVlacZ-infected C57BL/6 mice, in a 96-well plate at different effector-to-target ratios. Supernatants were collected after 24 hours and the amount of released $^{51}$Cr measured using a g counter. Spontaneous release of $^{51}$Cr was determined by incubating $^{51}$Cr-labeled target cells with medium alone and maximum release determined by adding sodium dodecyl sulfate (SDS) to a final concentration of 0.05%. The percentage of specific $^{51}$Cr release was calculated as follows:

Percent specific lysis =

$$\frac{(\text{experimental }^{51}Cr \text{ release} - \text{spontaneous }^{51}Cr \text{ release})}{(\text{maximum }^{51}Cr \text{ release} - \text{spontaneous }^{51}Cr \text{ release})}$$

EXAMPLE 10

Figure 1:
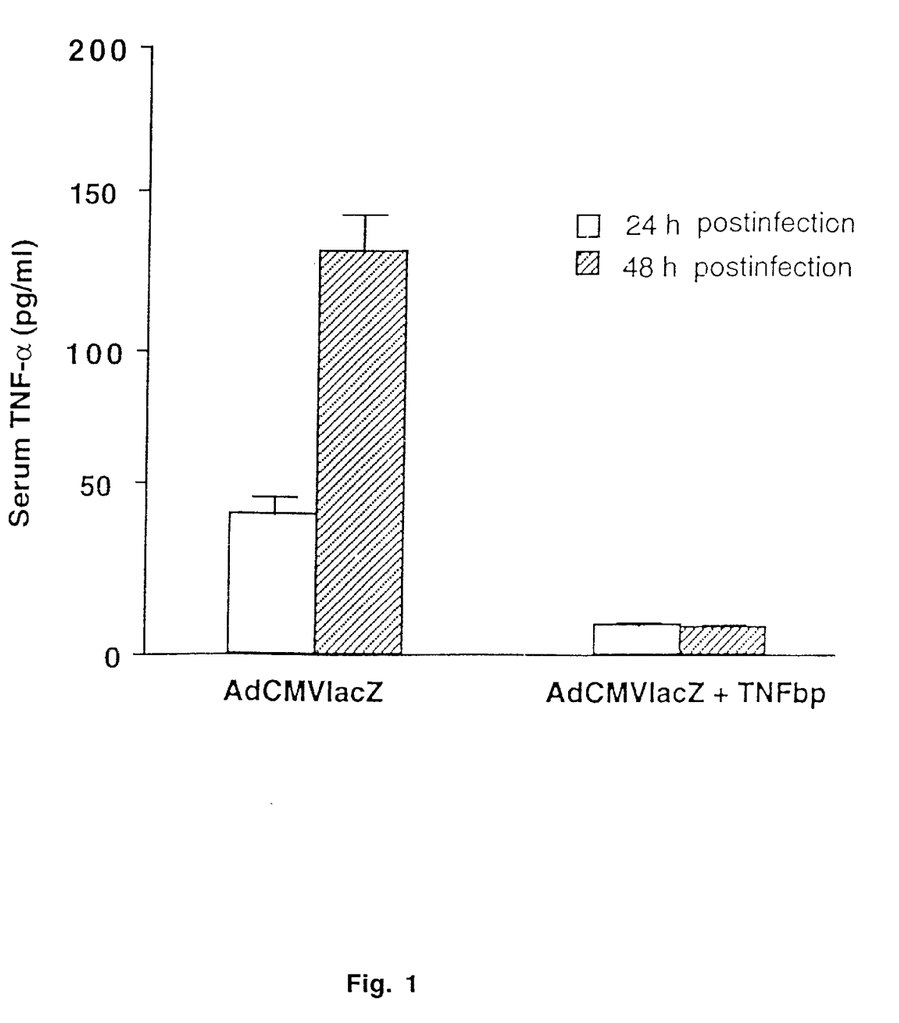

Treatment with TNF-bp Reduces Serum TNF-α Levels in AdCMVlacZ Virus-infected Mice AdCMVlacZ virus (1×10¹⁰ p.f.u., I.V.) was administered to TNFbp or control treated C57BL/6-+/+ mice. There was a significant increase in the serum levels of TNF at 24 hr and 48 hr in control mice (FIG. 1). Treatment of the AdCMVlacZ virus-infected C57BL/6-+/+ mice with TNF-bp (5 mg/kg body weight, intraperitoneally, every other day) resulted in reduced levels of TNF-α (less than 10 pg/ml) in the serum of TNF-bp-treated mice 24 hr after administration of AdCMVlacZ (FIG. 1). Thus, TNF-α is rapidly induced by adenovirus and this is neutralized by TNF-bp treatment.

EXAMPLE 11

Figure 2A:
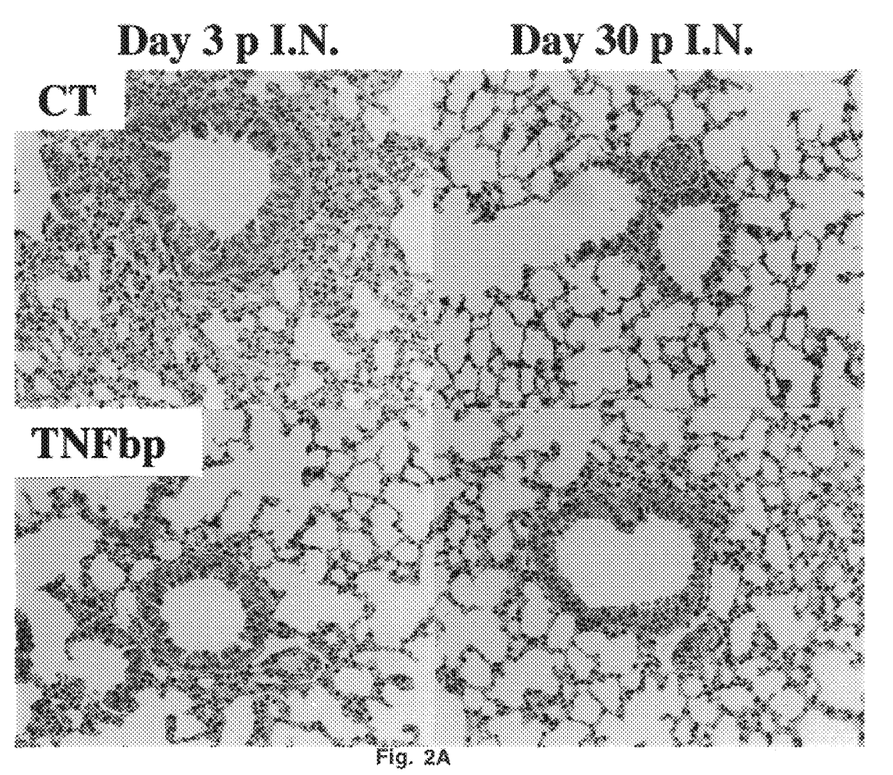
FIGS. 2A and 2B show the pulmonary inflammatory infiltration and β-Gal expression after intranasal administration of AdCMVlacZ. Lung tissue from vehicle-treated C57BL/6-+/+ mice, C57BL/6-+/+mice treated with TNF-bp, and were examined 3 and 30 days after intranasal administration of AdCMVlacZ ($1\times10^{10}$ p.f.u.). Tissue was fixed and stained with either hematoxylin and eosin or frozen sections were prepared for analysis of β-Gal staining.

Treatment with TNF-bp Decreases Liver and Lung Cellular Infiltration and Prolongs Expression of AdCMVlacZ After Intranasal and Intravenous Administration The effect of treatment with TNF-bp on inflammation of the lung and viral clearance after intransal administration of AdCMVlacZ (1×10¹⁰ p.f.u.) was evaluated. Three days after intranasal administration, there was a moderate inflammatory infiltrate in the lungs of control (CT)-treated C57BL/6-+/+ mice, which peaked at day 7, and was nearly resolved by day 30 (FIG. 2A; Table 1). In contrast, 3 days after administration of AdCMVlacZ, there was no evidence of an inflammatory infiltrate in the lungs of TNFbp treated C57BL/6-+/+ mice and only minimal evidence of infiltrates were observed from day 3 through day 30.

Figure 6:
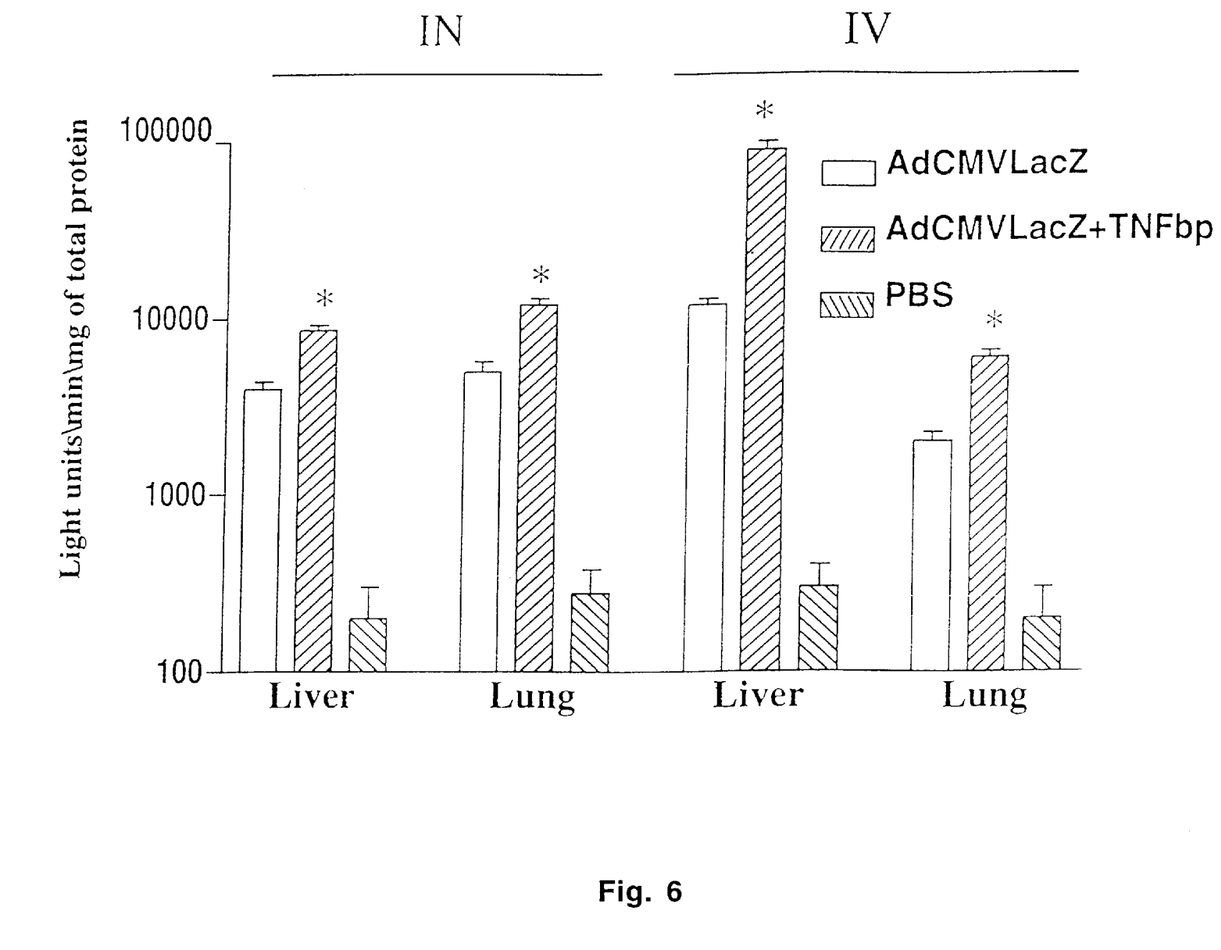
FIG. 6 shows the β-Gal expression in liver and lung 7 days after intravenous (IV) and intranasal (IN) administration of AdCMVlacZ. Liver and lung tissue from vehicle-treated C57BL/6 mice and from C57BL/6 mice treated with TNF-bp was examined 7 days after intravenous administration of AdCMVlacZ. Tissue was prepared for analysis of β-Gal activity as described below. The results represent the mean±SEM of five mice analyzed separately. Astericks (*) indicate a statistically significant difference in expression of β-Gal in TNF-bp-treated mice compared with control vehicle-treated mice.

There was high expression of lacZ in both the liver and lung after intranasal administration (FIG. 6). After intravenous administration of AdCMVlacZ (1×10¹⁰ PFU) there was increased expression of lacZ in the liver and less than 5% of the lacZ expression in the lung. Administration of TNF-bp resulted in an approximately 5- to 10-fold increase in lacZ expression in both liver and lung. Therefore, intranasal administration efficiently delivers AdCMVlacZ to both liver and lung, intravenous administration is not as an efficient way to deliver AdCMVlacZ to the lung, and TNF-bp increased expression in both liver and lung after administration.

TABLE 1

Inflammation and β-Gal Expression in the Lung and Liver of B6 mice at Different Times After AdCMVlacZ

| Tissue | Route[+] | Treatment[±] | Day 3 Inflammation* | Day 3 β-Gal* | Day 7 Inflammation | Day 7 β-Gal | Day 21 Inflammation | Day 21 β-Gal | Day 30 Inflammation | Day 30 β-Gal |
|---|---|---|---|---|---|---|---|---|---|---|
| Lung | I.N. | vehicle | $2^+$ | $2^+$ | $4^+$ | $4^+$ | $3^+$ | $2^+$ | $2^+$ | $1^+$ |
| Lung | I.N. | TNF-bp | 0 | $3^+$ | $1^+$ | $4^+$ | $1^+$ | $3^+$ | $1^+$ | $3^+$ |
| Liver | I.V. | vehicle | $1^+$ | $2^+$ | $2^+$ | $4^+$ | $1^+$ | 0 | $1^+$ | 0 |
| Liver | I.V. | TNF-bp | 0 | $2^+$ | 0 | $4^+$ | 0 | $3^+$ | 0 | $3^+$ |
| Liver | I.N. | vehicle | 0 | $2^+$ | $1^+$ | $4^+$ | 0 | $1^+$ | 0 | $1^+$ |
| Liver | I.V. | TNF-bp | 0 | $2^+$ | 0 | $4^+$ | 0 | $3^+$ | 0 | $2^+$ |
| Lung | I.V. | vehicle | $1^+$ | $2^+$ | $4^+$ | $4^+$ | $2^+$ | $1^+$ | $1^+$ | 1 |
| Lung | I.V. | TNF-bp | 0 | $2^+$ | $1^+$ | $4^+$ | 0 | $3^+$ | 0 | $3^+$ |

[+]Mice were infected with AdCMVlacZ administered both I.V.-intravenous or I.N.-intranasal
[±]TNF-bp; 1ug PEG-linked TNF-RI given I.V. q.o.d., vehicle control; PBS
*Inflammation was scored on a 0 (not present) to $4^+$ (maximum severity).
At least 5 mice were analyzed in each group.
βGal. β-galactosidase was quantitiated by determining the percentage of cells expressing β-Gal in at least 10 randomly chosen fields
The fields of view were scored using the following scale: $0 = <1\%$, $1^+ = <5\%$, $2^+ = <10\%$, $3^+ = <25\%$ and $4^+ = <50\%$.

Figure 2B:
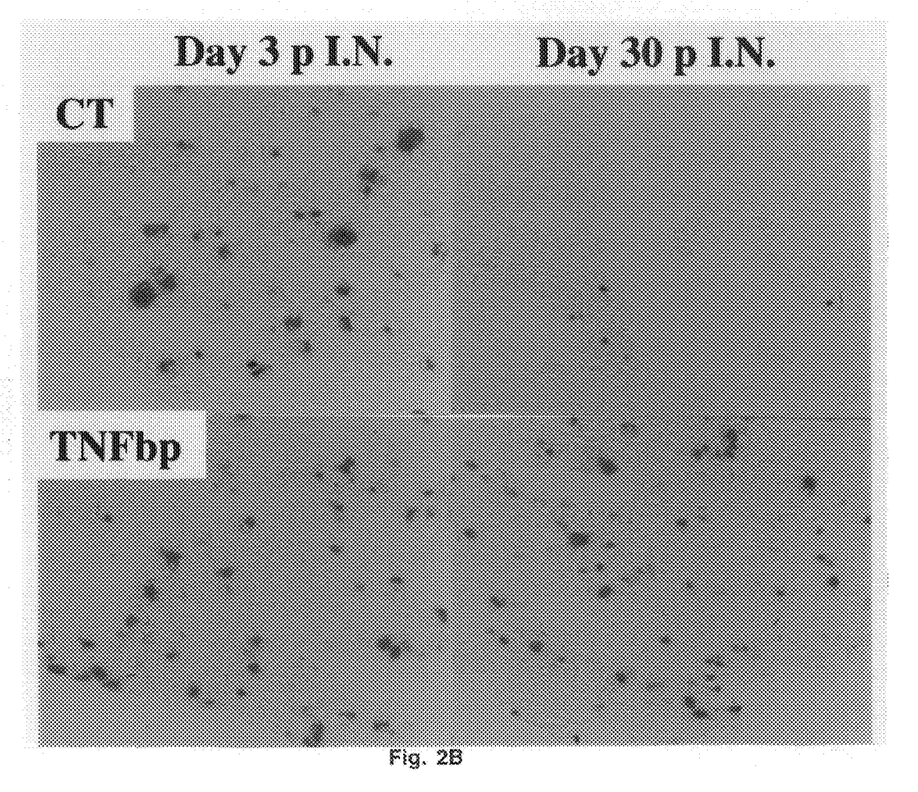

The expression of the lacZ adenovirus gene-therapy product was determined (FIG. 2B). The results indicated that the expression of β-gal in control-treated C57BL/6-+/+ mice reached its highest levels by day 7, but was considerably reduced by day 21 and remained at low levels through day 30 (FIG. 2B, Table 1). The expression of the β-gal in TNF-bp-treated C57BL/6-+/+ mice also peaked at day 7, but, in contrast to the control-treated mice, the expression of β-gal remained high in the lung through day 30.

Figure 3A:
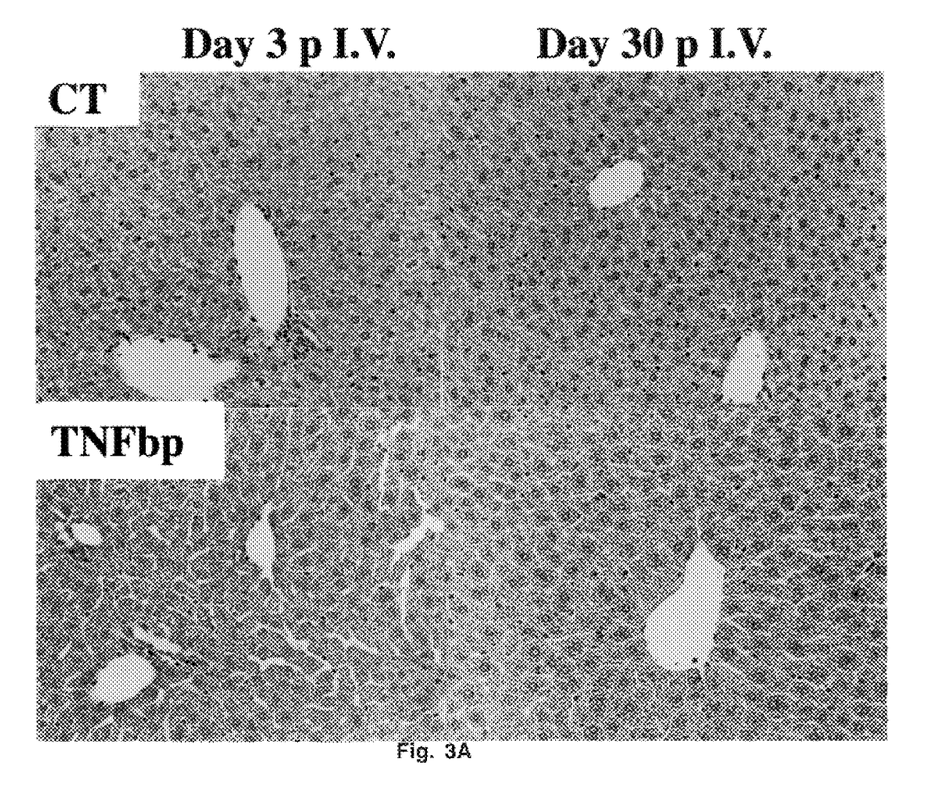
FIGS. 3A and 3B show the liver inflammatory response and β-Gal expression after intravenous administration of AdCMVlacZ. Liver tissue from vehicle-treated C57BL/6-+/+ mice and C57BL/6-+/+ mice treated with TNF-bp was examined 3 and 30 days after intravenous administration of AdCMVlacZ. Tissue was fixed and stained with either hematoxylin and eosin or frozen sections were prepared for analysis of β-Gal activity.
Figure 3B:
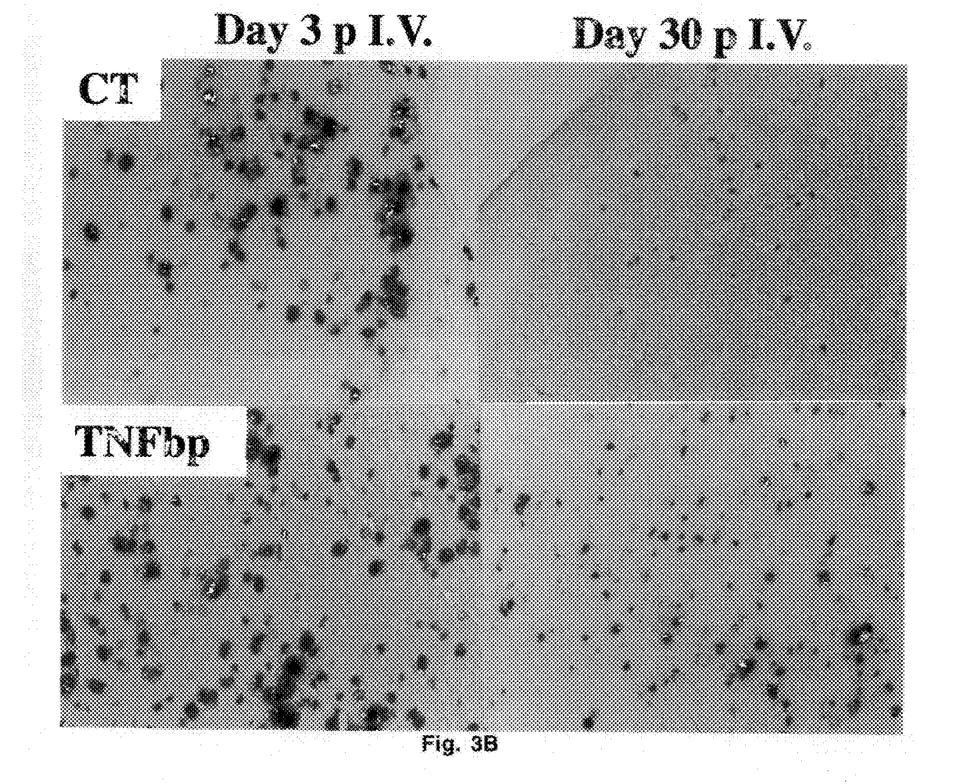

EXAMPLE 12
Treatment with TNF-bp Decreases Liver Cellular Infiltration and Prolongs Expression of AdCMVlacZ After Intravenous Administration Three days after intravenous administration, there was a moderate inflammatory infiltrate in the liver of vehicle-treated C57BL/6-+/+ mice, which peaked at day 7, and was nearly resolved by day 30 (FIG. 3A; Table 1). The inflammatory infiltrate of control-treated C57BL/6-+/+ mice appeared to consist of mononuclear cells in small clusters around the portal vein, around the portal triad, and also within the parenchyma not associated with vessels. By day 7 moderate numbers of small foci of inflammatory cells were observed and these had resolved by day 21. In contrast, there was no evidence of an inflammatory infiltrate in the liver of TNFbp treated C57BL/6-+/+ mice 3 days after administration of adenovirus, there was only minimal evidence of infiltrates observed from day 3 through day 30. Examination of liver tissue sections for expression of the lacZ adenovirus gene-therapy product indicated that the expression of the β-gal in control-treated C57BL/6-+/+ mice was highest by day 7, but reduced by day 21 and day 30 (FIG. 3B, Table 1). TNF-bp-treated C57BL/6-+/+ mice exhibited high expression of β-galactosidase through day 30.

Figure 4:
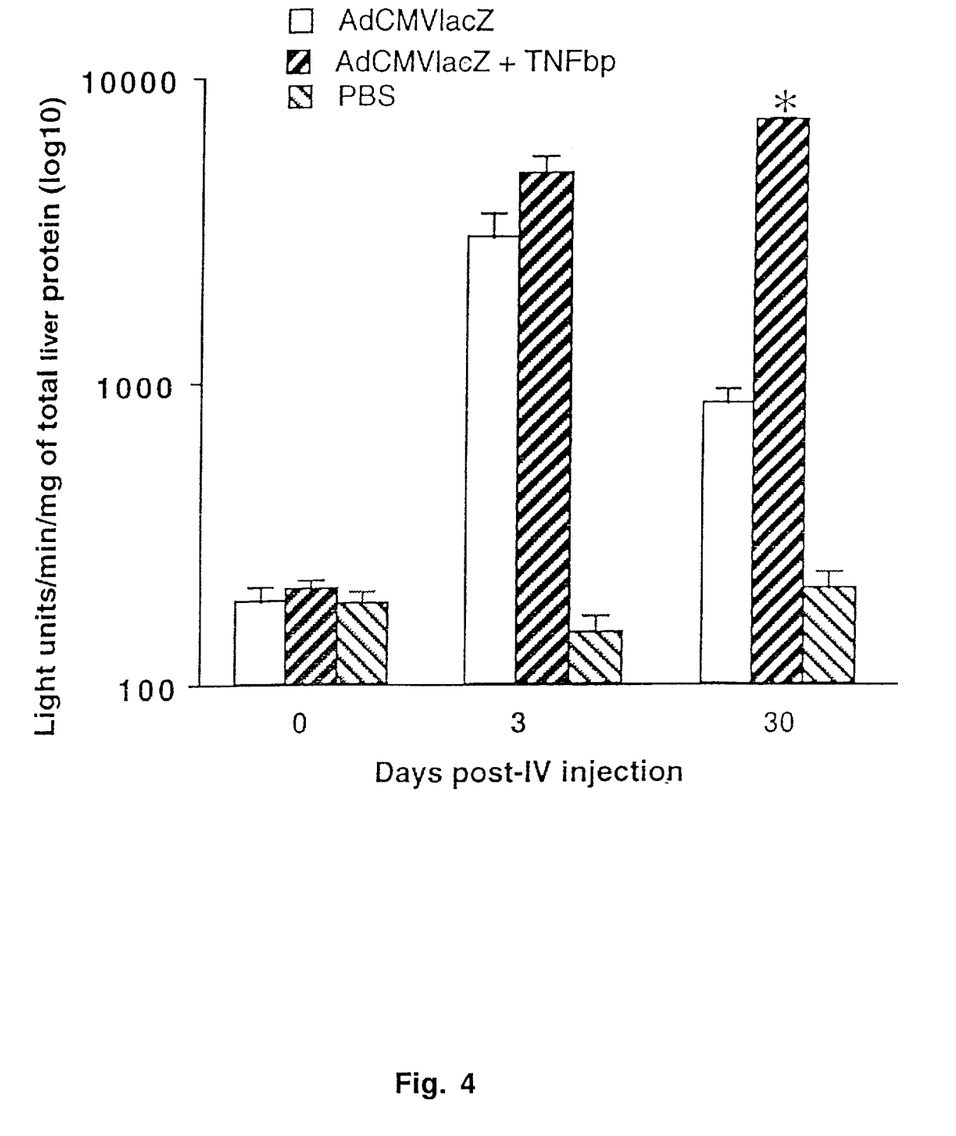
FIG. 4 shows the liver β-Gal expression after intravenous administration of AdCMVlacZ. Liver tissue from vehicle-treated C57BL/6-+/+ mice and C57BL/6-+/+ mice treated with TNF-bp was examined 0, 3 and 30 days after intravenous administration of AdCMVlacZ. Tissue was prepared for analysis of β-Gal activity, as described below.
Figure 5:
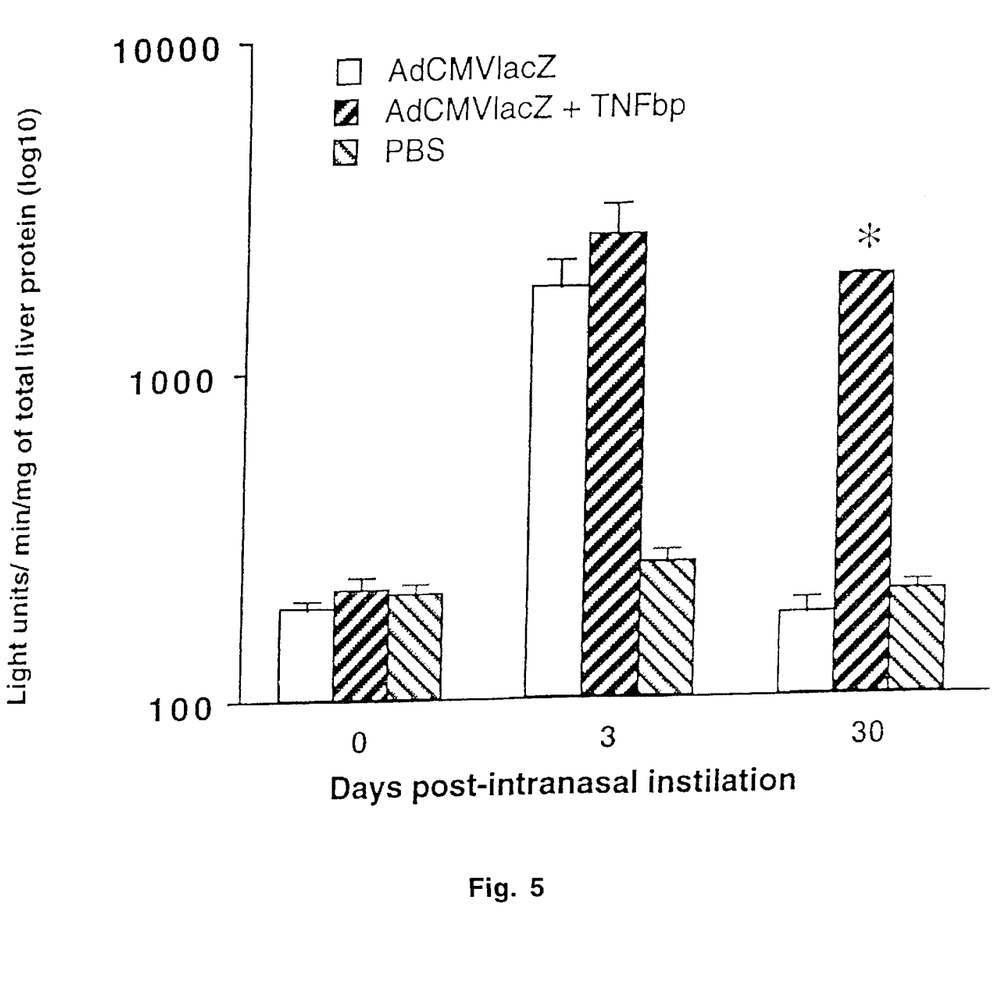
FIG. 5 shows liver β-Gal expression after intranasal administration of AdCMVlacZ. Liver tissue from vehicle-treated C57BL/6-+/+ mice and C57BL/6-+/+ mice treated with TNF-bp was examined 0, 3 and 30 days after intranasal administration of AdCMVlacZ. Tissue was prepared for analysis of β-Gal activity, as described below.

EXAMPLE 13
Treatment with TNF-bp Results in Increased Expression of AdCMVlacZ in the Liver After Intravenous and Intranasal Administration To quantitatively evaluate the inhibition of the clearance of the virus and prolong LacZ expression by TNFbp, liver tissue was also evaluated on days 0, 3, and 30 after intravenous (i.v.) and intranasal (i.n.) administration, respectively. Freshly isolated liver tissue was homogenized and the supernatant was assayed for β-galactosidase activity using a chemiluminescent reporter assay. The activity is expressed as the relative light units/min/mg of total protein in the liver. TNFbp treatment led to prolonged expression of the adenovirus LacZ gene after both intravenous and intranasal administration (FIGS. 4, 5) (p<0.05). Intranasal administration in combination with TNF-bp treatment resulted in optimal reduction of inflammation and highest β-gal expression.

To determine if iintranasal administration of adenovirus would induce a milder inflammatory response in the liver while still eliciting high levels of tropism of adenovirus to the liver tissue, recombinant AdCMVlacZ ($1\times10^{10}$ p.f.u.) was administered intranasal Compared to i.v. administration, the inflammatory response to intranasal administration of the AdCMVlacZ virus was lower in the livers of vehicle-treated C57BL/6-+/+ mice 3 and 7 days after intranasal administration, and not detectable between day 7 and 30 (Table 1).

EXAMPLE 14
Treatment with TNF-bp Decreases Lung Cellular Infiltration and Prolongs Expression of AdCMVlacZ After Intravenous Administration Intravenous administration of AdCMVlacZ results in high tropism of virus and expression of LacZ in the lung at days 3 and 7 in both control and TNFbp treated mice (Table 1). In both TNFbp and control treated mice, intravenous administration of AdCMVlacZ resulted in lower inflammation compared to intranasal administration at 21 and 30 days after administration. In TNFbp treated mice, this resulted in high expression of LacZ equivalent to that observed in mice receiving AdCMVlacZ intranasal and treated with TNFbp (Table 1).

Figure 7A:
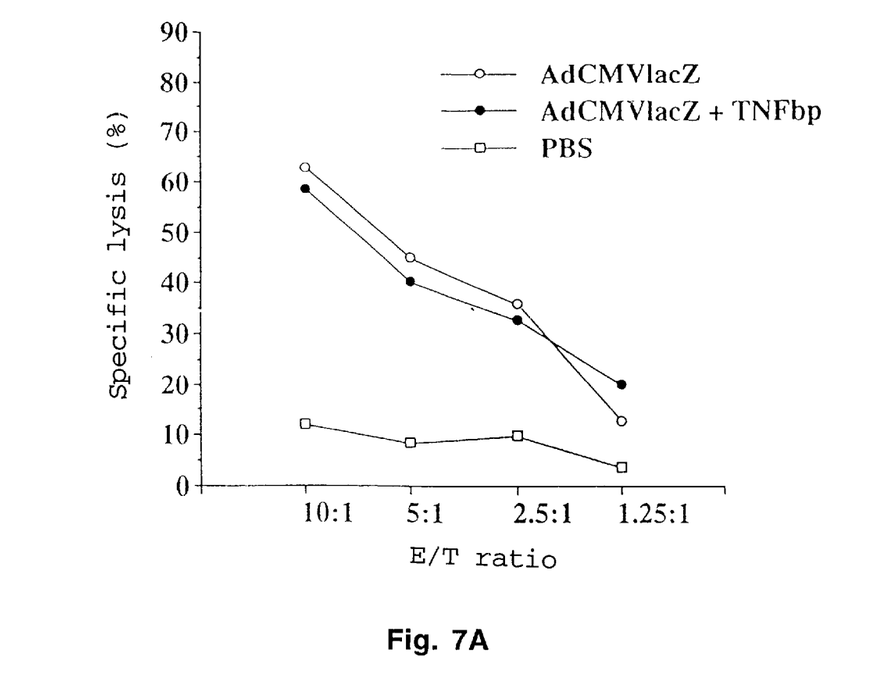
FIG. 7A shows the anti-adenovirus cytotoxic T cell response that was determined on day 16 after AdCMVlacZ virus administration.
Figure 7B:
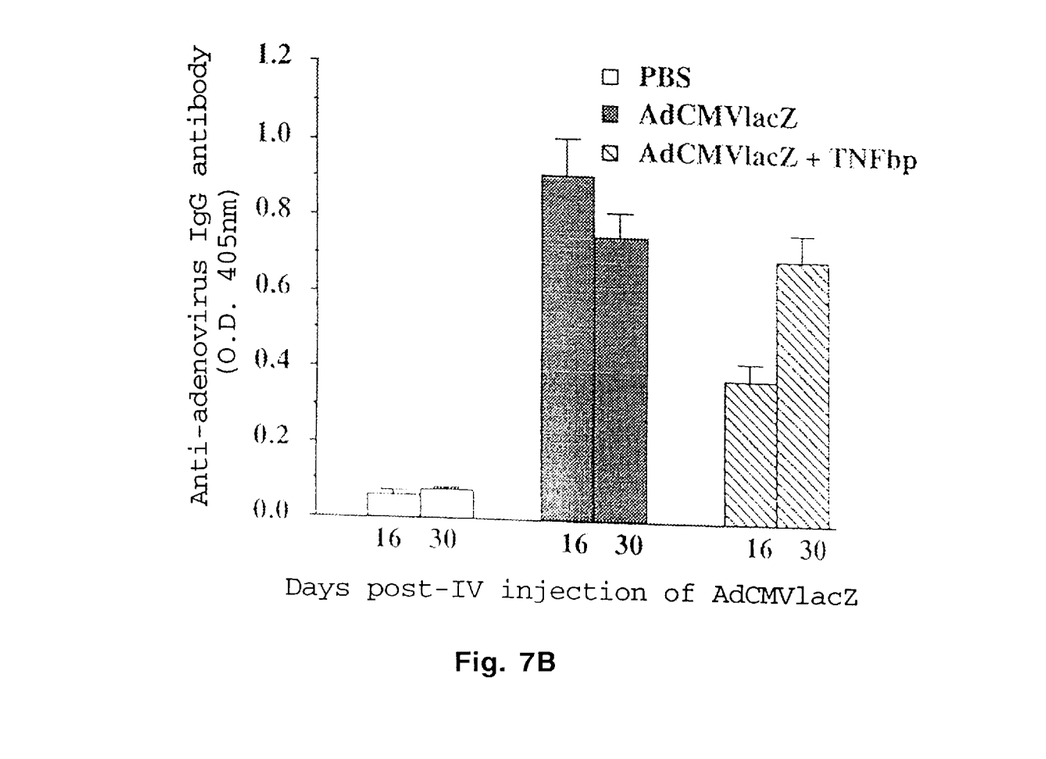
FIG. 7B shows the anti-adenovirus response that was determined on days 16 and 30 after AdCMVlacZ virus administration.

EXAMPLE 15
Cytotoxic T Cell Response and Anti-adenovirus Antibody After Intravenous Administration of AdCMVlacZ The anti-adenovirus cytotoxic T cell and antibody response of AdCMVlacZ virus infected mice with and without TNF-bp treatment was determined. There was no significant difference between the cytotoxic T cell response in TNF-bp treated mice compared with control mice 16 days after injection with AdCMVlacZ (FIG. 7A). There was a decrease in the antibody response on day 16 after TNF-bp treatment, but by day 30 there was no significant difference in the antibody response to adenovirus when comparing TNF-bp-treated with control treated mice (FIG. 7B).

This study establishes that treatment with TNF-bp significantly reduces inflammation and prolongs gene therapy.

This effect occurred in both the lung and liver after either intranasal or intravenous administration of the AdCMVlacZ recombinant virus. The TNF-bp therapy prolongs adenovirus expression of LacZ in the lung and liver for 4 weeks which is comparable to, or longer, than other anti-cytokine therapies directed at blocking IL-6, IL-10, IL-12, and IFN-α (Yang et al.,1995b; Kass-Eisler et al.,1996; Yang et al., 1996b; Yang and Wilson, 1995c).

The effectiveness of the TNF-bp in amelioration of inflammation and prolongation of the expression of the adenovirus may directly reflect the role of TNF-α in inflammation. TNF-α is produced primarily by macrophages, whereas IL-6, IL-10, and IFN-γ are produced primarily by T cells. Macrophages are the initial cell type involved in clearance of adenovirus and presentation of processed adenovirus to T cells. TNF-α is also the earliest cytokine produced by macrophages, followed by IL-1 and IL-12, and potentiates both the non-specific inflammatory response as well as the later, specific T-cell immune response.

It should be possible to produce adenovirus gene therapy with dual action of producing an effective sTNFR molecule and a desired gene therapy product. An Ad/TNFR vector which produces a chimeric protein capable of binding and neutralizing TNF and lymphotoxin, has been expressed in mice (Kolls et al.,1994). The recombinant adenovirus contained a fusion protein consisting of the human 55-kDa TNF receptor extracellular domain and the mouse IgG heavy chain domain (Ad/TNFRI). Within 3 days following the injection of $1 \times 10^9$ infectious particles, the TNF inhibitor concentration exceeded 1 mg/ml of plasma; this level of expression was maintained for at least 4 weeks. Administration of Ad/TNF-RI ($10^9$ p.f.u., i.v.) afforded significant protection to a lethal challenge with lipopolysaccharide with or without D-galactosamine (Kolls et al.,1995). sTNFR was readily detectable in the lung and was associated with decreased neutrophil recruitment and bacterial killing after intratracheal lipopolysaccharide or Pseudomonas aeruginosa respectively.

Inhibition of TNF-α prolongs the expression of β-gal in the recombinant AdCMVlacZ virus but did not inhibit the humoral immune response to the adenovirus (data not shown) as inhibition of the initial non-specific inflammatory component of the response to the adenovirus would not inhibit anti-vis antibody production. Although production of anti-viral antibodies is not an important factor in the clearance of the adenovirus after administration of a single dose, it plays an important role in the clearance of adenovirus on subsequent dosing. Most gene therapies require administration of multiple doses for induction of an effective response. Therefore, strategies to limit the B-cell response would have to be incorporated with the anti-TNF therapy to permit repeated administration of the adenovirus gene therapy.

The route of administration of adenovirus has been shown to affect the efficiency and immunogenicity of gene therapy delivery (Gahery-Segard et al., 1997; Van Ginkel et al., 1995). Oral tolerance to adenovirus results in decreased immunogenicity (Ilan et al., 1997). Intravenous, intraperitoneal, intranasal, and intrabiliary routes result in differences in delivery and immune response (Gahery-Segard et al., 1997; Van Ginkel et al., 1995). Intravenous administration of adenovirus results in higher titers and longer therapy in the lung compared to intranasal therapy. It is possible that intranasal administration evokes a more efficient pulmonary immune response by activation of the mucosal immune system, whereas intravenous administration and subsequent tropism of the adenovirus to the lung minimizes this inflammatory response. These results indicate that a non-natural route of administration of adenovirus may minimize the inflammatory response and prolong adenovirus gene therapy.

The following references were cited herein:

ABRAHAM, E., COULSON, W. F., SCHWARTZ, M. D., and ALLBEE, J. (1994). Effects of therapy with soluble tumor necrosis factor receptor fusion protein on pulmonary cytokine expression and lung injury following hemorrhage and resuscitation. Clin. Exp. Immunol. 98, 29–34.

COUTELIER, J. P., VAN BROECK, J., and WOLF, S. F. (1995). Interleukin-12 gene expression after viral infection in the mouse. J. of Virology. 69:1955–1958.

DAY, D. B., ZACHARIADES, N. A., and GOODING, L. R. (1994). Cytolysis of adenovirus-infected murine fibroblasts by IFN-gamma-primed macrophages is TNF- and contact-dependent. Cell. Immunol. 157, 223–238.

DELGADO, C., FRANCIS, G. E., and FISHER, D. (1992) The uses and properties of PEG-linked proteins. Critical Reviews in Therapeutic Drug Carrier Systems 9:249–304.

DEMATTEO, R. P., MARKMANN, J. F., KOZARSKY, K. F., BARKER, C. F., and RAPER, S. E., (1996). Prolongation of adenoviral transgene expression in mouse liver by T lymphocyte subset depletion. Gene Therapy. 3:4–12.

DERYCKERE, F., EBENAU-JEHLE, C., WOLD, W. S., and BURGERT, H. G. (1995). Tumor necrosis factor alpha increases expression of adenovirus E3 proteins. Immuno. Biol. 193, 186–192.

ENGLEMANN, H., HOLTMANN, H., BRAKEBUSCH, C., AVNI, Y. S., SAROV, I., NOPHAR, Y., HADAS, E., LEITNER, O., and WALLACH, D. (1990) Antibodies to a soluble form of a tumor necrosis factor (TNF) receptor have TNF-like activity. J Bio Chem 265:14497–14504.

EVANS, R. J., MCCABE, J. B., BENDELE, A. M., KIEFT, G. L., MCABEE, T. J., and EDWARDS, C. K. III, (1996). Efficacy of tumor necrosis factor binding protein (TNF-bp) in streptococcal cell wall-induced reaction model of arthritis. Arthritis Rheum 39 (suppl. 9):S284.

FISHER, C. J., JR., AGOSTI, J. M., OPAL, S. M., LOWRY, S. F., BALK, R. A., SADOFF, J. C., ABRAHAM, E., SCHEIN, R. M., and BENJAMIN, E. (1996). Treatment of septic shock with the tumor necrosis factor receptor: Fc fusion protein. The Soluble TNF Receptor Sepsis Study Group. New Engl. J. Med. 334, 1697–1702.

FISHER, K. J., JOOSS, K., ALSTON, J., YANG, Y., HAECKER, S. E., HIGH, K., PATHAK, R., RAPER, S. E., and WILSON, J. M. (1997). Recombinant adeno-associated virus for muscle directed gene therapy. Nature Medicine. 3:306–312.

GAHERY-SEGARD, H., JUILLARD, V., GASTON, J., LENGAGNE, R., PAVIRANI, A., BOULANGER, P., and GUILLET, J. G. (1997). Humoral immune response to the capsid components of recombinant adenoviruses: routes of immunization modulate virus-induced Ig subclass shifts. Eur. J. of Immunology. 27:653–659.

GAO, G. P., YANG, Y., and WILSON, J. M. (1996). Biology of adenovirus vectors with E1 and E4 deletions for liver-directed gene therapy. J. of Virology. 70:8934–8943.

GRAHAM, F. L., and PREVEC, L. (1995) Methods for construction of adenovirus vectors. Mol. Biotechnology 3:207–220.

GUERETTE, B., VILQUIN, J. T., GINGRAS, M., GRAVEL, C., WOOD, K. J., and TREMBLAY, J. P. (1996). Prevention of immune reactions triggered by first-generation adenoviral vectors by monoclonal antibodies and CTLA4Ig. Human Gene Therapy. 7:1455–1463.

HAAK-FRENDSCHO, M., STERS, S. A., MORDENTI, J., BRADY, S., GILLETT, N. A., CHEN, S. A., and ASHKENAZI, A. (1994). Inhibition of TNF by a TNF receptor immunoadhesin. Comparison to an anti-TNF monoclonal antibody. J. Immunol. 152, 1347–1353.

HE, X. S., CHEN, H. S., CHU, K., RIVKINA, M., and ROBINSON, W. S. (1996). Costimulatory protein B7-1 enhances the cytotoxic T cell response and antibody response to hepatitis B surface antigen. Proc. Natl. Acad. Sci. USA. 93:7274–7278.

ILAN, Y., ATTAVAR, P., TAKAHASHI, M., DAVIDSON, A., HORWITZ, M. S., GUIDA, J., CHOWDHURY, N. R., and CHOWDHURY, J. R. Induction of central tolerance by intrathymic inoculation of adenoviral antigens into the host thymus permits long-term gene therapy in Gunn rats. J. Clin. Invest. 98:2640–7, 1996.

ILAN, Y., PRAKASH, R., DAVIDSON, A., JONA., DROGUETT, G., HORWITZ M. S., CHOWDHURY, N. R., and CHOWDHURY, J. R. (1997). Oral tolerization to adenoviral antigens permits long-term gene expression using recombinant adenoviral vectors. J. Clinical Investigation. 99:1098–1106.

JOOSS, K., YANG, Y., and WILSON, J. M. (1996). Cyclophosphamide diminishes inflammation and prolongs transgene expression following delivery of adenoviral vectors to mouse liver and lung. Hum. Gene Therapy. 7:1555–1566.

KASS-EISLER, A., LEINWAND, L., GALL, J., BLOOM, B. and FALCK-PEDERSEN, E.,(1996). Circumventing the immune response to adenovirus-mediated gene therapy. Gene Therapy. 3:154–162.

KATRE, N. V., (1990) Immunogenicity of recombinant IL-2 modified by covalent attachment of polyethylene glycol. J Immunol 144:209–213.

KAY, M. A., MEUSE, L., GOWN, A. M., LINSLEY, P., HOLLENBAUGH, D., ARUFFO, A., OCHS, H. D., and WILSON, C. B. (1997). Transient immunomodulation with anti-CD40 ligand antibody and CTLA4Ig enhances persistence and secondary adenovirus-mediated gene transfer into mouse liver. P.N.A.S.. 94:4686–4691.

KOLLS, J., PEPPEL, K., SILVA, M., and BEUTLER, B. (1994). Prolonged and effective blockade of tumor necrosis factor activity through adenovirus-mediated gene transfer. Proc. Natl. Acad. Sci. USA 91, 215–219.

KOLLS, J. K., LEI, D., NELSON, S., SUMMER, W. R., GREENBERG, S., and BEUTLER, B. (1995). Adenovirus-mediated blockade of tumor necrosis factor in mice protects against endotoxic shock yet impairs pulmonary host defense. J. Inf. Dis. 171, 570–575.

KORNER, H., FRITZSCHE, U., and BURGERT, H. G. (1992). Tumor necrosis factor alpha stimulates expression of adenovirus early region 3 proteins: implications for viral persistence. Proc. Natl. Acad. Sci. USA 89, 11857–11861.

RABINOVICI, R., FEUERSTEIN, G., ABDULLAH, F., WHITEFORD, M., BORBOROGLU, P., SHEIKH, E., PHILLIP, D. R., OVADIA, P., BOBROSKI, L., BAGASRA, O., and NEVILLE L. F. (1996). Locally produced tumor necrosis factor-alpha mediates interleukin-2-induced lung injury. Circ. Res. 78, 329–336.

RANHEIM, T. S., SHISLER, J., HORTON, T. M., WOLD, L. J., GOODING, L. R., and WOLD, W. S. Characterization of mutants within the gene for the adenovirus E3 14.7-kilodalton protein which prevents cytolysis by tumor necrosis factor. J. Virol. 67, 2159–2167.

SAWCHUK, S. J., BOIVIN, G. P., DUWEL, L. E., BALL, W., BOVE, K., TRAPNELL, B., and HIRSCH R. (1996). Anti-T cell receptor monoclonal antibody prolongs transgene expression following adenovirus-mediated in vivo gene transfer to mouse synovium. Hum. Gene Therapy 7, 499–506.

SCHOWALTER D B. TUBB J C. LIU M. WILSON C B. KAY M A, (1997). Heterologous expression of adenovirus E3-gp19K in an E1a-deleted adenovirus vector inhibits MHC I expression in vitro, but does not prolong transgene expression in vivo. Gene Therapy. 4:351–360.

SMITH, C A, FARRAH T, and GOODWIN R G. (1994). The TNF receptor superfamily of cellular and viral proteins: activation, co-stimulation, and death. Cell 76, 959–962.

SMITH, T. A., WHITE, B. D., GARDNER, J. M., KALEKO, M., and MCCLELLAND, A. (1996). Transient immunosuppression permits successful repetitive intravenous administration of an adenovirus vector. Gene Therapy. 3:496–502.

TUFARIELLO, J. M., CHO, S., and HORWITZ, M. S. (1994). Adenovirus E3 14.7-kilodalton protein, an antagonist of tumor necrosis factor cytolysis, increases the virulence of vaccinia virus in severe combined immunodeficient mice. Proc. Natl. Acad. Sci. USA 91, 10987–10991.

VAN GINKEL, F. W., LIU, C., SIMECKA, J. W., DONG, J. Y., GREENWAY, T., FRIZZELL, R. A., KIYONO, H., MCGHEE, J. R., and PASCUAL, D. W., (1995). Intratracheal gene delivery with adenoviral vector induces elevated systemic IgG and muscosal IgA antibodies to adenovirus and beta-galactosidase. Hum. Gene Therapy 6, 895–903.

VILQUIN, J. T., GUERETTE, B., KINOSHITA, I., ROY, B., GOULET, M., GRAVEL, C., ROY, R., and TREMBLAY, J. P. (1995). FK506 immunosuppression to control the immune reactions triggered b y first-generation adenovirus-mediated gene transfer. Hum. Gene Therapy. 6:1391–1401.

WOLD, W. S. (1993). Adenovirus genes that modulate the sensitivity of virus-infected cells to lysis by TNF. J. Cell. Biochem. 53, 329–335.

WOOLEY, P. H., DUTCHER, J., WIDMER, M. B., and GILLIS, S. (1993). Influence of a recombinant human soluble tumor necrosis factor receptor FC fusion protein on type II collagen-induced arthritis in mice. J. Immunol. 151, 6602–6607.

WRIGHT, M., GRIM, J., DESHANE, J., KIM, M., STRONG, T. V., SIEGAL, G. P., and CURIEL, D. T. (1997) An intracellular anti-erbB-2 single-chain antibody is specifically cytotoxic to human breast carcinoma cells overexpressing erbB-2. Gene Therapy. 4:317–322.

SU, X., ZHOU, T., YANG, P., EDWARDS, C. K., III, and MOUNIZ, J. D. (1998). Soluble TNF receptor reduces arthritis and pneumonitis in motheaten mice. *Arthritis Rheum.* 41:(In Press).

YANG, Y., XIANG, Z,. ERTL, H. C., and WILSON, J. M. (1995a). Upregulation of class I major histocompatibility complex antigens by interferon gamma is necessary for T-cell-mediated elimination of recombinant adenovirus-infected hepatocytes in vivo. Proc. Natl. Acad. Sci. USA. 92:7257–7261.

YANG, Y., TRINCHIERI, G., and WILSON, J. M. (1995b). Recombinant IL-12 prevents formation of blocking IgA antibodies to recombinant adenovirus and allows repeated gene therapy to mouse lung. Nature Med. 1, 890–893.

YANG, Y., and WILSON, J. M. (1995c). Clearance of adenovirus-infected hepatocytes by MHC class I-restricted CD4+ CTLs in vivo. J. of Immunology. 155:2564–2570.

YANG, Y., SU, Q., GREWAL, I. S., SCHILZ, R., FLAVELL, R. A., and WILSON, J. M. (1996a). Transient subversion of CD40 ligand function diminishes immune responses to adenovirus vectors in mouse liver and lung tissues. J. of Virology. 70:6370–6377.

YANG, Y., GREENOUGH, K., and WILSON, J. M. (1996b). Transient immune blockade prevents formation of neutralizing antibody to recombinant adenovirus and allows repeated gene transfer to mouse liver. Gene Therapy. 3:412–420.

YANG, Y., SU, Q., and WILSON, J. M. (1996c). Role of viral antigens in destructive cellular immune responses to adenovirus vector-transduced cells in mouse lungs. J. of Virol. 70:7209–7212.

YANG, Y., JOOSS, K. U., SU, Q., ERTL, H. C., and WILSON, J. M. (1996d). Immune responses to viral antigens versus transgene product in the elimination of recombinant adenovirus-infected hepatocytes in vivo. Gene Therapy. 3:137–144.

YOUNG, D. C., KINGSLEY, S. D., RYAN, K. A., and DUTKO, F. J. (1993). Selective inactivation of eukaryotic (-galactosidase in assays for inhibitors of HIV-1 TAT using bacteria (-galactosidase as a reporter enzyme. Anal. Biochem. 215:24–30.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of increasing adenoviral gene expression in a tissue of an animal exposed to adenovirus vector for the first time, comprising the step of administering to said animal a pharmacologically effective dose of tumor necrosis factor binding protein and the adenoviral vector.

2. The method of claim 1, wherein said tumor necrosis factor binding protein is a polyethylene glycol-linked dimer of tumor necrosis factor receptor type I (TNF-RI).

3. The method of claim 1, wherein said tumor necrosis factor binding protein is administered in a dose of from about 0.3 mg/kg to about 5.0 mg/kg.

4. The method of claim 1, wherein said tumor necrosis factor binding protein is administered intranasally.

5. The method of claim 1, wherein said tumor necrosis factor binding protein is administered intravenously.

6. The method of claim 1, wherein said tumor necrosis factor binding protein results in a decrease in serum tumor necrosis factor-α.

7. A method of reducing an inflammatory response associated with adenoviral administration in a tissue of an animal exposed to adenovirus vector for the first time, comprising the step of administering to said animal a pharmacologically effective dose of tumor necrosis factor binding protein and the adenoviral vector.

8. The method of claim 7, wherein said tumor necrosis factor binding protein is a polyethylene glycol-linked dimer of tumor necrosis factor receptor type I (TNF-RI).

9. The method of claim 7, wherein said tumor necrosis factor binding protein is administered in a dose of from about 0.3 mg/kg to about 5.0 mg/kg.

10. The method of claim 7, wherein said tumor necrosis factor binding protein is administered intranasally.

11. The method of claim 7, wherein said tumor necrosis factor binding protein is administered intravenously.

12. The method of claim 7, wherein said tumor necrosis factor binding protein results in a decrease in serum tumor necrosis factor-α.

* * * * *